Jan. 1, 1952 L. B. BOELLNER Plant Pat. 1,063

WALNUT TREE

Filed Nov. 17, 1949

Inventor:
L. B. Boellner
By Robb & Robb, Attorneys

Patented Jan. 1, 1952

Plant Pat. 1,063

UNITED STATES PATENT OFFICE 1,063

WALNUT TREE

Louis B. Boellner, Roswell, N. Mex., assignor to Stark Bro's Nurseries And Orchards Company, Louisiana, Mo., a corporation of Missouri Application November 17, 1949, Serial No. 127,978

1 Claim. (Cl. 47—62)

The present invention relates to a new and distinct variety of walnut tree, originating as a seedling from a nut which was produced on a black walnut tree to which I had applied pollen from a Persian (English) walnut.

This new variety, while it resembles the black walnut in general appearance, is distinguished therefrom in that it has a pointed and slightly cleft base, thereby presenting a characteristically different shape. This nut is further characterized as to novelty by its very thin shell, light color of the kernel, ease with which the kernels may be removed from the shell in quarters and halves, the very plumpness of the kernel which fills the shell tightly, and the mild walnut flavor of the meat.

In its growth habit, the new variety tree is very hardy, enabling it to withstand severe climates where the temperature varies from very high to very low.

This new variety has been asexually reproduced by grafting and budding in Butler and Sedgwick Counties, Kansas, and Chaves County, New Mexico.

Figure 1:
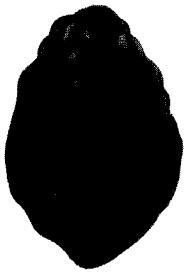
Figure 1 is an edge elevation of a nut of this new variety.
Figure 2:
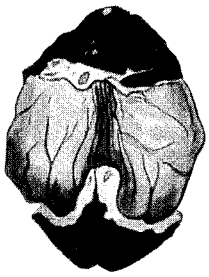
Figure 2 is a view with part of the shell cut away to show the kernel and plump character thereof.
Figure 3:
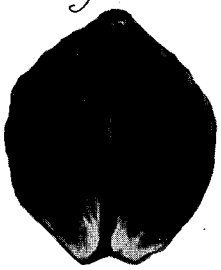
Figure 3 is a front elevation of the nut showing more particularly its cleft base.
Figure 4:
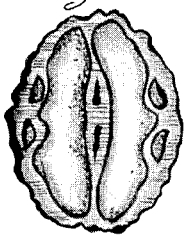
Figure 4 is a horizontal section through a nut.
Figure 5:
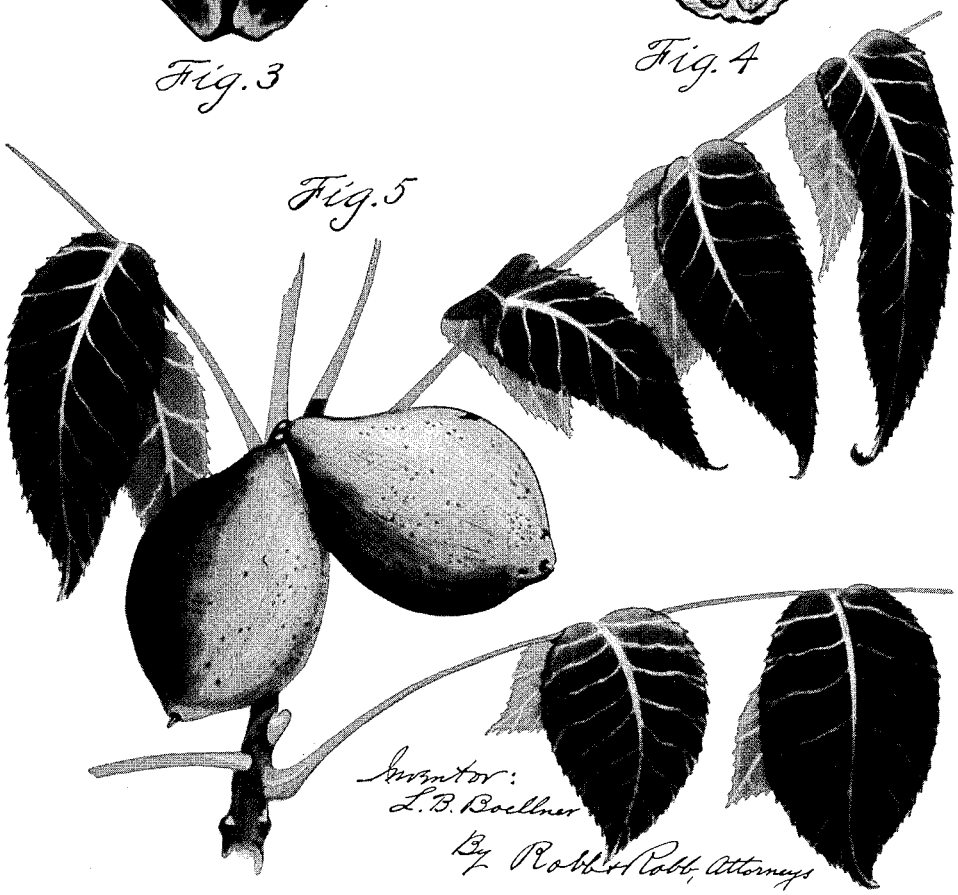
Figure 5 is a fragmentary portion of a branch with foliage and growing nuts (in their hulls).

Asexual reproduction of this new variety shows the foregoing characteristics come true to form and are established.

The specimens described were grown at Roswell, New Mexico.

The following is a detailed description of the new variety:

Dates of first and last picking—September 1st–September 15th.

Seedling:
- *Seed parent.*—Selected black walnut. (Unpatented.)
- *Pollen parent.*—Persian walnut. (Unpatented.)

Maturity season: Date—September 1–September 15 in Sedgwick County, Kansas. Nuts require two to three weeks to cure properly, after gathering.

Tree: Large; vigorous; hardy.
- *Productivity.*—Medium productive.
- *Growth habit.*—Vigorous.
- *Limbs.*—Slim.
- *Foliage.*—Moderately abundant; leaflets finely serrate.
- *Buds.*—Pointed; pubescent.

Nuts:
- *Ripening.*—Even. Time of harvesting—September 1st to September 15th.
- *Quantity.*—Medium abundant.
- *Maturity.*—Early.
- *Tenacity.*—Cling.
- *Cluster.*—Size—medium. Average number of nuts to cluster, 2.
- *Size.*—Length—1¾ inches. Diameter—1⅛ x 1⅜ inches.
- *Weight.*—Average number of nuts to pound, 25.
- *Shape.*—Base—cuneate. Point—mucronate.
- *Shell.*—Thin. Cracks and releases—easy.

Kernel:
- *Flavor.*—Good.
- *Shape.*—Round mucronate with wide space between lobes at base.
- *Texture.*—Firm.
- *Sutures.*—Even.

Resistance to: Insects and diseases — medium good.

I claim:

A new and distinct variety of walnut tree characterized as to novelty by its hardiness to withstand extremes of temperature; its production of nuts in general appearance similar to a black walnut but having a very thin shell; very plump kernel which fills the shell tightly and which can be removed with ease in quarters and halves; the light color of the kernel, and the mild walnut flavor thereof, substantially as herein shown and described.

LOUIS B. BOELLNER.

REFERENCES CITED

The following references are of record in the file of this patent:

UNITED STATES PATENTS

| Number | Name | Date |
|---|---|---|
| Pl. Pt. 494 | Schafer et al. | Dec. 16, 1941 |